United States Patent
Yarbrough et al.

(10) Patent No.: US 6,423,746 B1
(45) Date of Patent: Jul. 23, 2002

(54) URUSHIOL INDUCED CONTACT DERMATITIS AND METHOD OF USE

(75) Inventors: William M. Yarbrough, Peoria; Corey Schroeter, East Peoria, both of IL (US)

(73) Assignee: The William M. Yarbrough Foundation, Peoria, IL (US)

( * ) Notice: Subject to any disclaimer, the term of this patent is extended or adjusted under 35 U.S.C. 154(b) by 0 days.

(21) Appl. No.: 09/347,714

(22) Filed: Jul. 3, 1999

(51) Int. Cl.$^7$ ................... A61K 31/195; A61K 31/20
(52) U.S. Cl. ................ 514/561; 514/862; 514/558
(58) Field of Search ........................ 424/401, 472, 424/59, 862; 514/167, 255, 25, 558, 53, 561

(56) References Cited

U.S. PATENT DOCUMENTS

| | | | |
|---|---|---|---|
| 3,862,331 A | 1/1975 | Crary | 424/331 |
| 3,875,301 A | 4/1975 | Windheuser | 424/45 |
| 3,922,342 A | 11/1975 | Rathbun | 424/79 |
| 4,002,737 A | 1/1977 | Borris | 424/94 |
| 4,259,318 A | 3/1981 | Duhe et al. | 424/94 |
| 4,499,086 A | 2/1985 | Garren | 424/195 |
| 4,663,151 A | 5/1987 | Waali | 424/45 |
| 4,917,890 A | 4/1990 | McAnalley | 424/195 |
| 5,011,689 A | 4/1991 | Misenko | 424/195 |
| 5,620,527 A * | 4/1997 | Kramer et al. | 134/2 |
| 5,653,965 A * | 8/1997 | Narayanan et al. | 424/59 |
| 5,686,074 A | 11/1997 | Stewart | 424/195 |
| 5,789,399 A * | 8/1998 | Strube | 514/167 |
| 5,814,338 A * | 9/1998 | Veronesi | 424/472 |
| 5,833,999 A * | 11/1998 | Trinh et al. | 424/401 |
| 5,888,520 A * | 3/1999 | Toma et al. | 424/401 |

OTHER PUBLICATIONS

Poison Ivy, Sumac & Oak, American Academy of Dermatology, 1993 *Protect Yourself from Poison Ivy*, Isadora B. Stehlin, Consumers' Research v.80, No. 8, pp30–1.
*Poison Ivy Dermatitis*, Rudolf L. Baer, Cutis, V. 46, Jul. 1990, pp34–6.

* cited by examiner

Primary Examiner—William R. A. Jarvis
Assistant Examiner—Vickie Kim

(57) ABSTRACT

A treatment for urushiol induced contact dermatitis is provided for in a topical treatment. According to the invention, a method is provided for applying a composition of substances to the effected area, working the composition into the effected area, and removing the composition from the effected area. The composition comprises at least one ethoxylate in combination with Sodium Lauryl Sarcosininate (or "SLS"). It is believed that this combination binds to the available urushiol receptors rendering it inactive. The affinity of the receptors for the ethoxylates also appears to cause a release of the urushiol from its epidermal bonds for bonding to the composition. An inert scrubbing agent, such as polyethylene beads, can also be included to assist in the release of the urushiol. Acetylated lanolin alcohol, sodium lauroyl sarconinate, EDTA, a foam stabilizer, and water can also be added to the composition without effecting performance.

8 Claims, No Drawings

URUSHIOL INDUCED CONTACT DERMATITIS AND METHOD OF USE

I. FIELD OF THE INVENTION

The present invention relates to treatments for allergic dermatitis and, more particularly, to a treatment for Toxicodendron dermatitis, which results from contact with the Rhus oleoresin urushiol.

II. BACKGROUND OF THE INVENTION AND PRIOR ART

Urushiol is the toxin responsible for the allergic dermatitis caused by contact with the sap of commonly encountered noxious plants such as poison ivy, poison oak, and poison sumac, and related plants found throughout the world. Urushiol or related chemicals are also found in the Anacardiaceae group, which includes, among others, the lacquer tree of Asia, mango tree, cashew shell oil, and in certain nut shells, such as the walnut.

The American Academy of Dermatology estimates that there are up to 50 million cases of urushiol induced contact dermatitis annually in the United States alone. No one is sure of the number of world wide annual exposures but some experts estimate that the number could be double that of the United States. Accordingly, urushiol induced contact dermatitis is a world wide problem.

Chemically, urushiols are mixtures of catechols with long, hydrophobic, carbon(alkyl) side chains at the three position of the catechol ring. For example, poison ivy contains predominantly 3-n-pentadececylcatechols (C-15) and poison oak contains predominantly 3-n-heptaecylcatechols (C-17). When located inside an unruptured plant leaf, Urushiol is a light, colorless oil. When exposed to oxygen, urushiol easily oxidizes and, after polymerizing, turns a blackish color.

The reaction is the result of exposure to the oleoresin containing the urushiol. The reaction is an allergic eczematous contact dermatitis characterized by redness, swelling, papules, vesicles, bullac, and streaking.

Treatment has historically consisted of attempting to remove the oil as quickly after exposure as possible: applying rubbing alcohol, washing effected areas with water, and showering with soap and water. Unfortunately, if the above procedure is not commence within minutes of exposure the regimen will not remove the toxin but may limit its spread.

Attempts have been made to find both prophylactic treatments as well as post-exposure treatments. To date, no vaccine has been developed and the prior art treatments are not without shortcomings. One treatment example is seen in U.S. Pat. No. 5,686,074 to Stewart which teaches and claims a treatment for poison ivy which includes a composition including linseed oil, an astringent, a starch, an essential oil and a citrus oil. One shortcoming of this patent is that linseed oil can cause irritation itself A second shortcoming of this patent is that it requires that the composition be applied to the effected areas up to twice a day until the rash is gone. The composition provides what appears to be only very temporary palliative relief of poison ivy symptoms and does not appear to alter the course of the malady.

Other proposed treatments are seen in U.S. Pat. Nos. 5,620,527, 5,011,689 4,499,086, 4,259,318, 4,002,737, 3,862,331, 3,875,301, and 3,922,342.

Yet other prior art attempts have focused on prophylactics for preventing the dermatitis. One example is seen is U.S. Pat. No. 4,663,151 to Waali which discloses and claims a prophylactic treatment based upon Aluminum Chlorhydrate. Of course, the most significant shortcoming associated with prophylactic treatments is that they are only effective if applied before exposure to the urushiol; an occurrence that rarely takes place.

A significant advance in the treatment of poison ivy is seen in an unpatented product sold under the mark Tech-Nu® and manufactured by Tec Laboratories, Inc. of Albany, Oreg. However, this product is not without shortcomings. This product was originally developed as a treatment for radiation exposure. It was discovered, however, that the product also provided some relief for poison ivy exposure. The main active ingredient in the Tech-Nu-® product is Octylphenoxy-polyethoxyethano. The four octyl groups of this chemical are to large too surround the non polar moieties in the urushiol. Therefore, it only partially matches the polarity of urushiol. Thus, the action of this product renders the urushiol only partially inactive. Since the urushiol remains partially active and continues to cause irritation, only temporary relief is provided and multiple applications are necessary. Also, the chemical makeup of the product requires that it be applied no later than eight hours after exposure to urushiol.

There is need, therefore, for a safe, effective treatment for dermatitis caused by exposure to the toxin urushiol. The treatment should provide complete relief from the signs and symptoms associated with the dermatitis in limited treatments and be effective at any point during the dermatitis cycle.

II. OBJECTS OF THE INVENTION

It is an object of the present invention to provide a treatment for urushiol induced allergic dermatitis, the treatment providing almost immediate and permanent relief in usually one treatment.

It is a further object of the present invention to provide such a treatment in a method that utilizes a composition that chemically attaches to available urushiol receptors to block its allergic reaction properties and to release the urushiol so that it can be removed from the skin.

It is yet another object of the present invention to provide a treatment for urushiol induced contact dermatitis that includes a first nonyl phenyl ethoxylate, a second nonyl phenyl ethoxylate, acetylated lanolin alcohol, sodium lauryl sarcosinate, EDTA, a foam stabilizer, water, and inert polyethylene granules.

It is a yet further object of the present invention to provide a treatment which is safe to use.

It is yet another object of the present invention to provide a treatment for urushiol induced allergic dermatitis which is topical, can be purchased over the counter and is economical.

IV. SUMMARY OF THE INVENTION

The above objects of the invention are provided for in a topical treatment for urushiol induced contact dermatitis. According to the invention, a method is provided for applying a composition of substances to the effected area, working the composition into the effected area, and removing the composition from the effected area. The composition comprises at least one ethoxylate in combination with Sodium Lauryl Sarcosinate or; "SLS"). It is believed that this combination binds to the available urushiol receptors rendering it inactive. The affinity of the receptors for the ethoxylates also appears to cause a release of the urushiol from its epidermal bonds for bonding to the composition. An inert scrubbing agent, such as polyethylene beads, can also be included to assist in the release of the urushiol. Acetylated lanolin alcohol sodium lauryl sarcosinate, EDTA, a foam stabilizer, and water can also be added to the composition without effecting performance.

V. DETAILED DESCRIPTION OF THE INVENTION

As noted above, urushiol is the toxin responsible for the contact dermatitis caused by poison ivy, poison oak, and other urushiol containing plants. When housed inside an unruptured plant leaf, urushiol is a fight, colorless oil. The leaves are easily damaged by the slightest contact or even breeze. Therefore, it is rare to find a plant that does not have at least some ruptured leaves. When exposed to oxygen, urushiol easily oxidizes and, after polymerizing, turns a blackish color.

The reaction experienced by most people is the result of exposure to the oleoresin containing the urushiol. The reaction is an allergic eczematous contact dermatitis characterized by redness, swelling, papules, vesicles, bullae, and streaking. Urushiol is the name given to a family catechols having long, hydrophobic, carbon(alkyl) side chains at the three position of the catechol ring. The chemical structure of the urushiol found in the poison ivy plant is:

OH
OH
$(CH_2)_7CH\ CH(CH_2)_5CH_2$

It is seen that the urushiol of the poison ivy plant contains predominantly 3-n-pentadececylcatechols (C-15). Poison oak is known to contain predominantly 3-n-heptaecylcatechols (C-17). Other urushiol containing plants contain catechols that have side chains of varying lengths.

It has been discovered that a hand scrub product manufactured and sold by the Redman Scientific, Company of Dallas, Tex. can alleviate the signs and symptoms of urushiol induced contact dermatitis. The product has been sold for approximately twenty years, and is known to be a safe, gentle hypoallergenic product. The product has been sold as an industrial hand cleaner and has never heretofore been known to be effective against urushiol toxicity. It has only been promoted as a hand cleaner.

Chemical analysis and research by the inventors has revealed that two of the component parts of the Redman product are central to its effectiveness as a treatment for urushiol induced contact dermatitis: an ethoxylate and Sodium Lauryl Sarcosinate. The ethoxylate is a nonylphenol ehtoxylate. Unlike the ethoxylate of the Tech-Nu® product, the present invention's ethoxylate has the large octyl groups removed. In this way, the ethoxylate can "wrap" around the non-polar molecules of the urushiol. Further, the long chain moiety of the present invention's ethoxylate is only four carbons long, as opposed to ten. This feature also assists the ethoxylate in bonding to the urushiol more effectively. However, the ethoxylate itself is not capable of forming a complete micelle around the urushiol. The inventors have discovered that the addition of Sodium Lauryl Sarcosinate, the micelle is completed and the urushiol can be cleansed away from the skin. SLS also has a long carbon chain that can surround the non-polar portions of the urushiol. In addition, SLS contains a highly polar end that aids in surrounding the polar ends of urushiol and also in the invention's reactivity with water.

Thus, the combination of the ethoxylate and SLS create a large molecule that contains flexible non-polar groups and soluble polar groups. This permits the inventive composition to quickly and effectively surround the urushiol and then be rinsed away with water, a highly polar substance.

The inventors have also discovered that the addition of an inert scrubbing agent improves the action of the inventive composition. The scrubbing agent assists by causing the urushiol to detach from the skin and place it in position for bonding with the active chemical components of the inventive composition. Any inert agent will suffice but the inventors believe that polyethylene beads work best. The beads should be large enough to be effective but not so large as to cause abrasions. The inventors suggest beads in the range of 5 to 50 microns with an average size being approximately 25 microns or 50 mesh.

To make the inventive composition, an exact ratio of ethoxylate to SLS is not critical. The only requirement is that the ethoxylate is completely reacted with the SLS, creating a polymer. This will vary with the ethoxylate used, but the inventors have determined that a ratio of ethoxylate-to- SLS of 1.5:2 is preferred. The amount by weight of polyethylene beads can vary according to the grittiness desired. The inventors have found that a formula of ethoxylate:SLS:polyethylene of 40:20:40 is preferred but that formulas of other concentrations are useful. Thus, for production purposes, formulas having SLS ranging from 10 to 20% by weight, ethoxylate ranging from 20 to 40% by weight, and polyethylene beads from 20 to 50% by weight are reasonable. But again, the formula is not restricted to these ranges, which ranges are presented for example purposes only.

Also, a cutting agent that does not chemically react with the composition may be added. The cutting agent makes the overall composition flow more easily, thereby enabling more packaging options such as tubes. The cutting agent must be added only in sufficient amount that it promotes flow but does not effect the action of the composition.

In use, the composition is applied to an effected area and worked over the area by a scrubbing motion. After sufficient time has elapsed to ensure that the effected area has been adequately exposed to the composition, the composition and bound urushiol are washed away. Experiments have demonstrated that a majority of people need only one treatment to be relieved of itching, however, severe cases may require two treatments approximately eight hours apart. The inventive composition works at varying rates of effectiveness at any time during the rash cycle.

We claim:

1. A method for treating contact dermatitis comprising the steps of:
   preparing a topical composition comprising a nonyl phenyl ethoxylate and sodium lauryl sarcosinate;
   applying the composition to an affected area;
   permitting the composition to remain on the affected area a sufficient amount of time to enable the composition of matter to cause an effect; and,
   removing the composition from the affected area.

2. The method of claim 1 wherein preparing the composition further includes adding second nonyl phenyl ethoxylate.

3. The method of claim 1 wherein preparing the composition further includes adding acetylated lanolin alcohol.

4. The method of claim 1 wherein preparing the composition further includes adding acetylated polyethylene granules.

5. The method of claim 1 wherein preparing the composition further includes adding water.

6. The method of claim 1 wherein preparing the composition further includes EDTA.

7. The method of claim 1 wherein preparing the composition further includes a foam stabilizer.

8. The method of claim 1 further including the step of adding a thinning agent to the composition.

* * * * *

UNITED STATES PATENT AND TRADEMARK OFFICE
CERTIFICATE OF CORRECTION

PATENT NO. : 6,423,746 C1
APPLICATION NO. : 90/007485
DATED : August 29, 2006
INVENTOR(S) : Yarbrough et al.

It is certified that error appears in the above-identified patent and that said Letters Patent is hereby corrected as shown below:

Column 2, line 4, delete "lauryl" and substitute -- lauroyl --.

Signed and Sealed this
Twenty-fourth Day of April, 2012

David J. Kappos
*Director of the United States Patent and Trademark Office*

(12) EX PARTE REEXAMINATION CERTIFICATE (5484th)
United States Patent
Yarbrough et al.

(10) Number: US 6,423,746 C1
(45) Certificate Issued: Aug. 29, 2006

(54) URUSHIOL INDUCED CONTACT DERMATITIS AND METHOD OF USE

(75) Inventors: William M. Yarbrough, Peoria, IL (US); Corey Schroeter, East Peoria, IL (US)

(73) Assignee: The William M. Yarbrough Foundation, Peoria, IL (US)

Reexamination Request:
No. 90/007,485, Mar. 28, 2005

Reexamination Certificate for:
Patent No.: 6,423,746
Issued: Jul. 23, 2002
Appl. No.: 09/347,714
Filed: Jul. 3, 1999

(51) Int. Cl.
*A61K 31/195* (2006.01)
*A61K 31/20* (2006.01)

(52) U.S. Cl. .................. 514/561; 514/862; 514/558
(58) Field of Classification Search .................. None
See application file for complete search history.

(56) References Cited

U.S. PATENT DOCUMENTS

| 3,862,331 A | 1/1975 | Crary |
| 3,875,301 A | 4/1975 | Windheuser |
| 3,922,342 A | 11/1975 | Rathbun |
| 4,002,737 A | 1/1977 | Borris |
| 4,199,575 A | 4/1980 | Gunther |
| 4,259,318 A | 3/1981 | Duhe et al. |
| 4,499,086 A | 2/1985 | Garren |
| 4,663,151 A | 5/1987 | Waali |
| 4,917,890 A | 4/1990 | McAnalley |
| 5,011,689 A | 4/1991 | Misenko |
| 5,620,527 A | 4/1997 | Kramer et al. |
| 5,653,965 A | 8/1997 | Narayanan et al. |
| 5,679,374 A * | 10/1997 | Fanchon et al. ............ 424/450 |
| 5,686,074 A | 11/1997 | Stewart |
| 5,730,967 A * | 3/1998 | Hill et al. ................ 424/78.01 |
| 5,789,399 A | 8/1998 | Strube |
| 5,814,338 A | 9/1998 | Veronesi |
| 5,833,999 A | 11/1998 | Trinh et al. |
| 5,888,520 A | 3/1999 | Toma et al. |
| 6,423,746 B1 | 7/2002 | Yarbrough et al. |

OTHER PUBLICATIONS

Poison Ivy, Sumac & Oak, American Academy of Dermatology, 1993 Protect Yourself from Poison Ivy, Isadora B. Stehlin, Consumers' Research v.80, No. 8 pp. 30–31.
Posion Ivy Dermatitis, Rudolf L. Baer, Cutis, V. 46, Jul. 1990, pp. 34–36.

* cited by examiner

Primary Examiner—Evelyn Mei Huang

(57) ABSTRACT

A treatment for urushiol induced contact dermatitis is provided for in a topical treatment. According to the invention, a method is provided for applying a composition of substances to the effected area, working the composition into the effected area, and removing the composition from the effected area. The composition comprises at least one ethoxylate in combination with Sodium Lauryl Sarcosininate (or "SLS"). It is believed that this combination binds to the available urushiol receptors rendering it inactive. The affinity of the receptors for the ethoxylates also appears to cause a release of the urushiol from its epidermal bonds for bonding to the composition. An inert scrubbing agent, such as polyethylene beads, can also be included to assist in the release of the urushiol. Acetylated lanolin alcohol, sodium lauroyl sarconinate, EDTA, a foam stabilizer, and water can also be added to the composition without effecting performance.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 5 is cancelled.

Claims 1, 2, 6 and 7 are determined to be patentable as amended.

Claims 3, 4 and 8, dependent on an amended claim, are determined to be patentable.

1. A method for treating *urushiol induced* contact dermatitis, comprising the steps of:

preparing a topical composition comprising a nonyl phenyl ethoxylate [and], sodium lauryl sarcosinate, *and water*;

applying the composition to an affected area;

permitting the composition to remain on the affected area a sufficient amount of time to enable the composition of matter to cause an effect; and[.]

removing the composition from the affected area.

2. The method of claim 1 wherein preparing the composition further includes adding *a* second nonyl phenyl ethoxylate.

6. The method of claim 1 wherein preparing the composition further includes *adding* EDTA.

7. The method of claim 1 wherein preparing the composition further includes *adding* a foam stabilizer.

* * * * *